United States Patent
Li

(10) Patent No.: US 6,517,486 B1
(45) Date of Patent: Feb. 11, 2003

(54) COMPOUNDING METHOD FOR REDUCING SPECKLE NOISE

(75) Inventor: Pai-Chi Li, Taipei (TW)

(73) Assignee: Computed Ultrasound Global, Inc. (TW)

( * ) Notice: Subject to any disclaimer, the term of this patent is extended or adjusted under 35 U.S.C. 154(b) by 33 days.

(21) Appl. No.: 09/930,931

(22) Filed: Aug. 16, 2001

(51) Int. Cl.$^7$ ................................................. A61B 8/00
(52) U.S. Cl. ...................................................... 600/443
(58) Field of Search ................................ 600/437, 443, 600/447; 382/128; 73/602

(56) References Cited

U.S. PATENT DOCUMENTS

| | | | | |
|---|---|---|---|---|
| 4,817,614 | A | * | 4/1989 | Hassler et al. ................. 73/625 |
| 5,178,147 | A | * | 1/1993 | Ophir et al. .................. 600/437 |
| 5,503,153 | A | * | 4/1996 | Liu et al. .................. 73/861.25 |
| 5,524,636 | A | * | 6/1996 | Sarvazyan et al. ............. 73/787 |
| 6,012,458 | A | * | 1/2000 | Mo et al. ..................... 600/437 |
| 6,102,865 | A | * | 8/2000 | Hossack et al. ............. 600/459 |
| 6,200,266 | B1 | * | 3/2001 | Shokrollahi et al. ........ 600/438 |
| 6,360,027 | B1 | * | 3/2002 | Hossack et al. ............. 382/294 |

OTHER PUBLICATIONS

H. E. Melton, Jr., P.A. Magnin; A–Mode Speckle Reduction with Compound Frequencies and Compound Bandwidths; *Ultrasonic Imaging;* 1984; pp. 159–173; vol. 6; Academic Press, Inc.; USA.

M. O'Donnell, S.D. Silverstein; Optimum Displacement for Compound Image Generation in Medical Ultrasound; *IEEE Transactions on Ultrasonics, Ferroelectrics, and Frequency Control;* Jul. 1988; pp. 470–476; vol. 35, No. 4; IEEE; USA.

P. C. LI; M. O'Donnell; Elevational Spatial Compounding; *Ultrasonic Imaging;* 1994; pp. 176–189; vol. 16; Academic Press, Inc.; USA.

* cited by examiner

*Primary Examiner*—Francis J. Jaworski
(74) *Attorney, Agent, or Firm*—Alston & Bird LLP

(57) ABSTRACT

A compounding method for reducing speckle noise applied in an ultrasound imaging apparatus is disclosed. The compounding method includes the steps of providing an object, measuring the object for obtaining a reference image by the ultrasound imaging apparatus, applying an external force to the object to deform the object, measuring the deformed object for obtaining an deformed object image at the same position, estimating an in-plane displacement field of the deformed object image for correcting an in-plane motion of the object to obtain a corrected image, and compounding the reference image with the corrected image to obtain a compounded image of the object for achieving the speckle noise reduction.

17 Claims, 5 Drawing Sheets

COMPOUNDING METHOD FOR REDUCING SPECKLE NOISE

FIELD OF THE INVENTION

The present invention relates to a compounding method for reducing speckle noise, and more particularly to a compounding method for reducing speckle noise applied in an ultrasound imaging apparatus.

BACKGROUND OF THE INVENTION

The inherent target-detection capability of coherent imaging system is severely degraded by the presence of speckle. Speckle is the result of constructive and destructive interference and appears as a random mottle superimposed on an image. Thus, it will obscure the detail of image. Hence, this degradation is especially objectionable in diffraction limited ultrasonic imaging system.

Speckle in coherent optical or acoustical images can be reduced by a number of methods including spatial compounding and frequency compounding methods. Furthermore, both spatial and frequency compounding methods are tried to achieve the speckle noise reduction by increasing the decorrelation between speckle patterns of the same object. For the spatial compounding method, the speckle decorrelation is achieved by imaging the same target object from different angles. That is, when the relative distance between the target object and the transducer of imaging apparatus is changed, the speckle decorrelation can be increased. On the other hand, for the frequency compounding method, the speckle decorrelation is achieved by imaging the same target object within different frequency ranges.

Those compounding methods according to the prior arts can increase the decorrelation to reduce the speckle noise in the image, however, the prior arts reduce the speckle noise at the price of significant degradation in spatial resolution. For the spatial compounding method, the spatial resolution will degrade because the beam size is increased in order to measure the target object from different angles. Similarly, the spatial resolution will degrade in the frequency compounding method, because the bandwidth is reduced to result in that the pulse becomes longer.

Therefore, the purpose of the present invention is to develop a compounding method to deal with the above situations encountered in the prior art.

SUMMARY OF THE INVENTION

It is therefore an object of the present invention to provide a compounding method for reducing speckle brightness variations of the image with less spatial resolution degradation.

It is another object of the present invention to provide a compounding method for reducing speckle noise by the decorrelation between signals under different strain states.

According to an aspect of the present invention, there is provided a compounding method for reducing speckle noise applied in an ultrasound imaging apparatus. The compounding method includes the steps of providing an object, measuring the object for obtaining a reference image by the ultrasound imaging apparatus, applying an external force to the object to deform the object, measuring the deformed object for obtaining a deformed object image at the same position, estimating an in-plane displacement field of the deformed object image for correcting an in-plane motion of the object to obtain a corrected image, and compounding the reference image with the corrected image to obtain a compounded image of the object for achieving the speckle noise reduction.

For example, the ultrasound imaging apparatus is a medical diagnostic ultrasound apparatus.

Preferably, the object is a tissue, an organ or an embryo.

Preferably, the reference image, the deformed object image, the corrected image and the compounded image are composed of a plurality of pixels, respectively. Each plural pixels of the compounded image is preferably an average of each relative plural pixels of the reference image and each relative plural pixels of the corrected image, respectively.

According to another aspect of the present invention, there is provided a compounding method for reducing speckle noise applied in an ultrasound imaging apparatus. The compounding method includes the steps of providing an object which spontaneously produces deformation, measuring the object for obtaining a first image at a first time, measuring the object for obtaining a second image at a second time at same position, wherein the second image is an image of the deformed object, estimating an in-plane displacement field of the second image for correcting an in-plane motion of the object to obtain a corrected image, and compounding the first image with the corrected image to obtain a compounded image of the object for achieving the speckle noise reduction.

For example, the ultrasound imaging apparatus is a medical diagnostic ultrasound apparatus.

Preferably, the object is a tissue, an organ or an embryo.

Preferably, the first image, the second image, the corrected image and the compounded image are composed of a plurality of pixels, respectively. Each plural pixels of the compounded image is preferably an average of each relative plural pixels of the first image and each relative plural pixels of the corrected image, respectively.

According to an additional aspect of the present invention, there is provided an ultrasound imaging apparatus. The apparatus includes a detector for measuring an object to obtain a reference image at a position and measuring the object having a deformation to obtain an deformed object image at the position, and a processor for estimating an in-plane displacement field of the deformed object image for correcting an in-plane motion of the object to obtain a corrected image, compounding the reference image with the corrected image to obtain a compounded image of the object for achieving speckle noise reduction, and outputting a signal of the compounded image.

For example, the ultrasound imaging apparatus is a medical diagnostic ultrasound apparatus.

Preferably, the object is a tissue, an organ or an embryo.

Preferably, the deformation of object is results from applying an external force or spontaneously producing.

Preferably, the reference image, the deformed object image, the corrected image and the compounded image are composed of a plurality of pixels, respectively. Each plural pixels of the compounded image is preferably an average of each relative plural pixels of the reference image and each relative plural pixels of the corrected image, respectively.

Preferably, the ultrasound imaging apparatus further includes a device for receiving the signal of compounded image, wherein the device is a display or a printer.

The present invention may best be understood through the following description with reference to the accompanying drawings, in which:

DETAILED DESCRIPTION OF THE PREFERRED EMBODIMENTS

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

Figure 1:
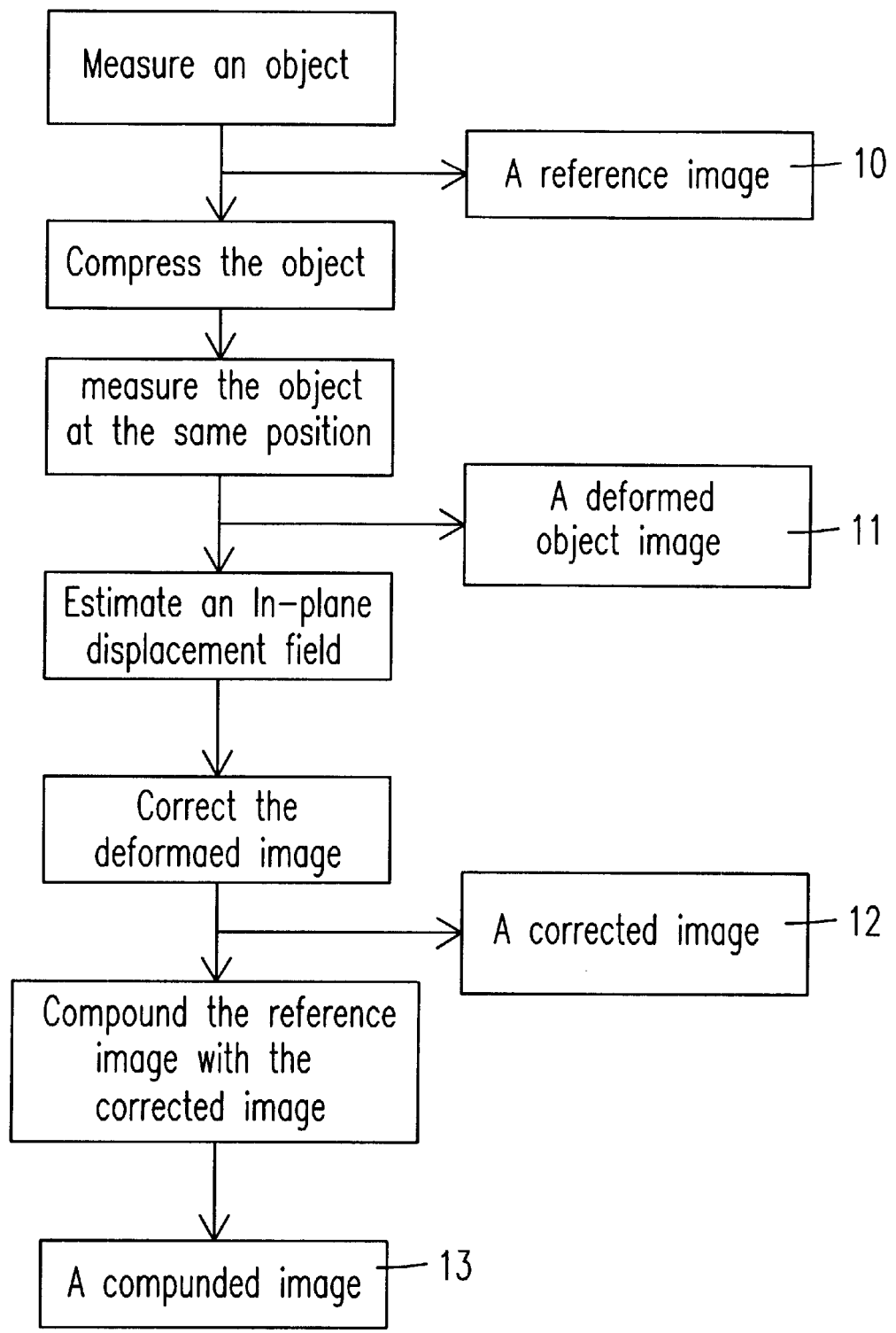
FIG. 1 is a flow chart illustrating a preferred embodiment of a compounding method for reducing speckle noise according to the present invention.

FIG. 1 is a flow chart illustrating a preferred embodiment of a compounding method for reducing speckle noise according to the present invention. First of all, an object, for example a human tissue, is measured to obtain a reference image 10 by an ultrasound imaging apparatus. Secondly, the object is compressed by an external force at the same position and measured to obtain a deformed object image 11. Sequentially, the deformed object image 11 is compared with the reference image 10 to estimate an in-plane displacement field and then the object motion is corrected to obtain a corrected image 12. Finally, the corrected image 12 is compounded with the reference image 10 in order to obtain a compounded image 13 of the object. The compounding step is an incoherent averaging of partially correlated measurements. Furthermore, if more than two measurements are available, the same procedures can be repeated and the speckle brightness variations can be further reduced.

Figure 2A:
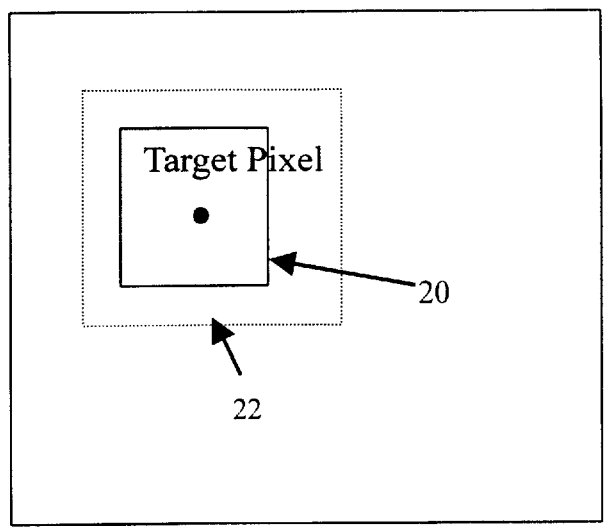
FIGS. 2A–2B are diagrams illustrating an estimating step of an in-plane displacement according to the present invention.
Figure 2B:
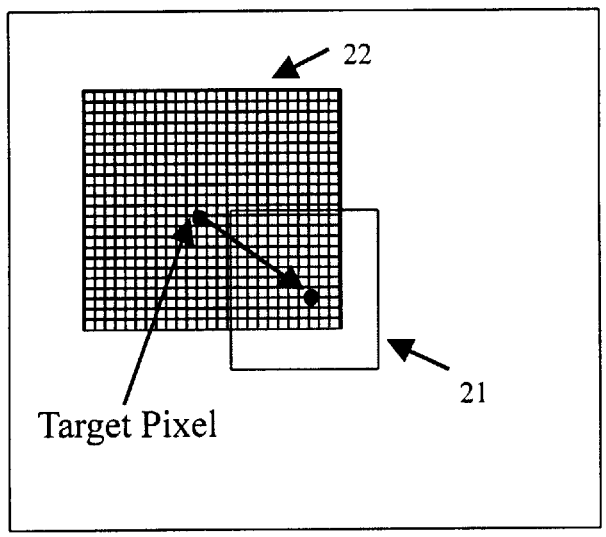

In addition, when the external force is applied to the object, the object is deformed to create a three-dimensional motion. Hence, the in-plane motion must be estimated and corrected to ensure that the reference image 10 and the deformed object image 11 used to be compounded are spatially matched. For estimating the in-plane motion, a two-dimensional speckle tracking shown in FIG. 2 is employed. During estimating, the high correlation between the reference image 10 and the deformed object image 11 is required for obtaining the accurate motion estimation. On the contrary, during compounding, the speckle reduction is relied on the decorrelation of signals. In other words, lower correlation is required to effectively reduce speckle brightness variations. However, the conflict between the accurate motion estimation and the effective speckle reduction can be solved by applying multiple incremental compressions. Hence, when using a small increment, two adjacent images are highly correlated and thus in-plane motion can be accurately estimated. The motion between two images separated by a large number of compression increments can be obtained by accumulating the motion estimated from adjacent images. Therefore, when combining the images separated by multiple increments, the significant speckle decorrelation is obtained and the speckle brightness variations are effectively reduced.

When the compounding method of the present invention is applied in the medical diagnostic ultrasound apparatus, the object can be an organ or an embryo. However, if the object can spontaneously produce deformation, such as a beating heart, the application of the external force can be omitted.

Hereinafter, an example is given to further describe the above embodiment so as to facilitate the understanding of the present invention. Referring to FIG. 2, a speckle tracking, such as a block matching method, is performed for the motion estimation and correction. Preferably, the two-dimensional speckle tracking is used to find the in-plane object motion resulting from the deformation. Furthermore, with the estimated motion, the images are spatially matched before being compounded. As shown in FIG. 2, the original image is referred to as the reference image and the deformed object image at a different strain is called the comparison image. Both the reference image and the comparison image are composed of plural pixels. Each pixel of the reference image is associated with an m by n matching block 20 around the pixel. The matching block 20 is compared to a group of candidate blocks 21 of the same size in the comparison image. The blocks 21 in the comparison image are within a pre-defined region around a target pixel in the reference image. This region is defined as a search window 22. For each pixel in the search window 22, a correlation coefficient between the matching block 20 and the candidate block 21 is calculated. The pixel in the comparison image with the highest correlation coefficient is considered the best match. Therefore, the displacement between the original pixel in the reference image and the best-matched pixel in the comparison image is defined as the estimated in-plane object motion for the target pixel. By assigning the value of the best-matched pixel to the target pixel position, the object motion is corrected. Furthermore, such a process is continued until the displacement fields for all pixels in the reference image are obtained.

Moreover, the three-dimensional object motion due to the object deformation is described by transforming the original position of a scatterer $(x_1, y_1, z_1)$ to a new position $(x_1', y_1', z_1')$. The two positions are related by the following equation $$(x_1', y_1', z_1') = (\alpha x_1, \beta y_1, \gamma z_1) \qquad (3)$$

It is required to ensure the object incompressibility, i.e. the constant total volume of the image object. In other words, the product of the three scaling factors must be unity, i.e. $\alpha\beta\gamma=1$. Assuming the object is compressed in the axial direction with a strain of $1-\alpha$, $$\beta = \gamma = \alpha^{-0.5} \qquad (4)$$

for an isotropic tissue. It can be easily shown that the change in spatial resolution, assuming that there are only two images used for compounding, is $(1+\alpha^{-1})/2$.

Figure 3:
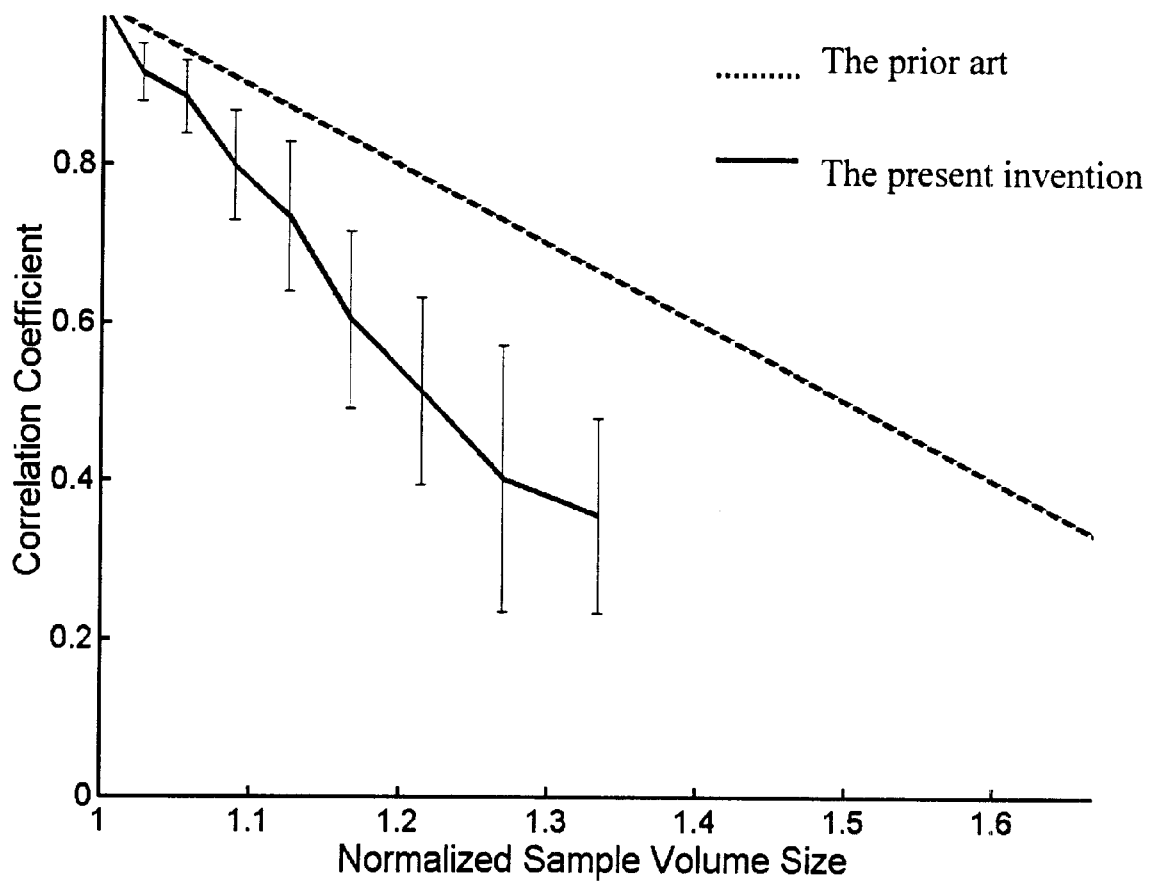
FIG. 3 is a plot illustrating a resolution comparison of the compounding method of the prior art with that of the present invention.

FIG. 3 is a plot illustrating a resolution comparison of the compounding method of the prior art with that of the present invention. Using simulations, the relation between the efficacy of speckle reduction and the change in spatial resolution is obtained, wherein the efficacy of speckle reduction is represented by correlation coefficient and the change in spatial resolution is represented by normalized sample volume size. As shown in FIG. 3, the relation between the correlation coefficient and the fractional sample volume change according to the compounding method of the prior art is approximately linear, which is represented by the dashed line. Generally, the correlation coefficient decreases from 1 to 0 while the sample volume size increases to twice of the original size. In addition, as shown in FIG. 3, the solid line represents the average correlation coefficients and the error bars indicate +/− one standard deviation according to the present invention. The result shows that the solid line is noticeably lower than the dashed line. In other words, the compounding method according to the present invention has lower correlation than that of the prior art with the same loss in the spatial resolution. Therefore, for the same loss in spatial resolution, the speckle noise according to the compounding method of the present invention is significantly reduced.

Figure 4:
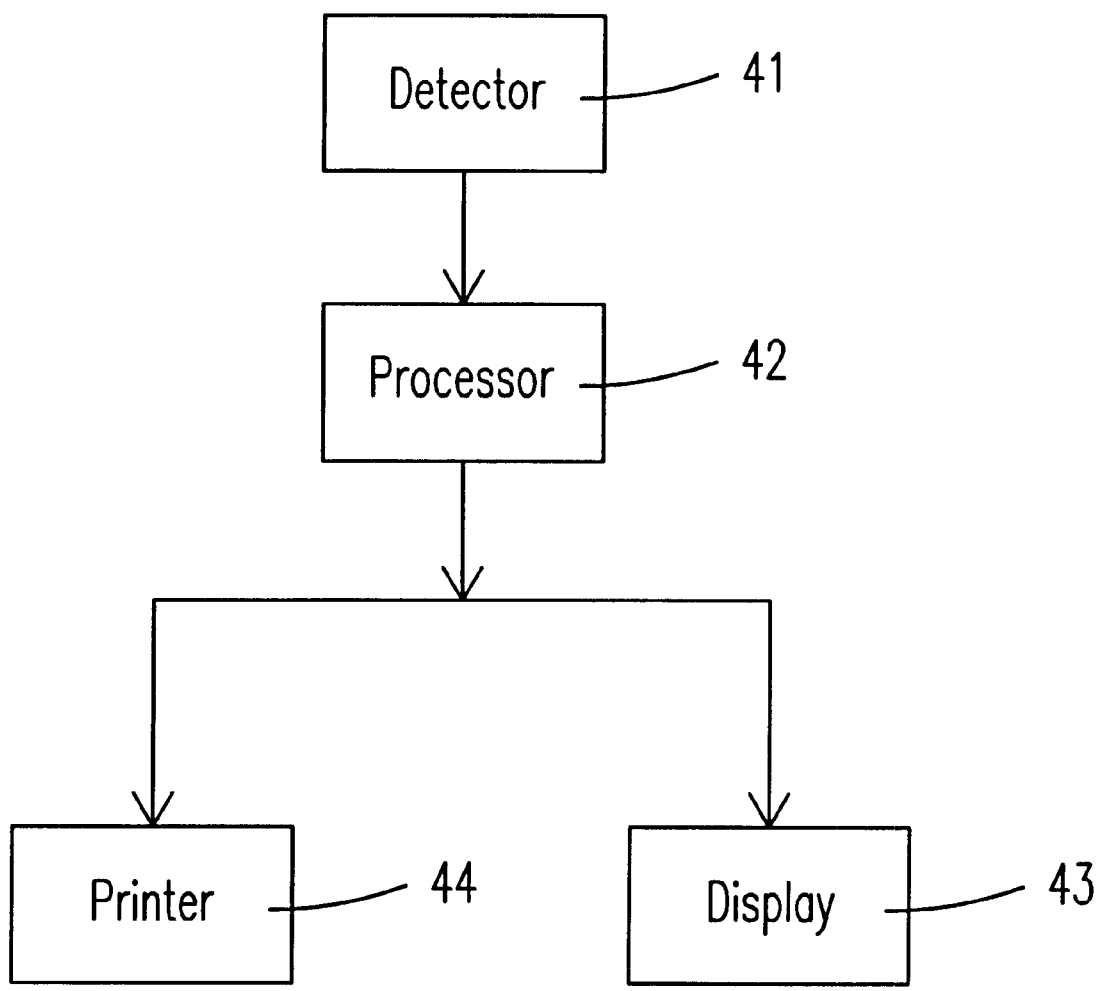
FIG. 4 is a diagram illustrating a function block of an ultrasound imaging apparatus according to the present invention.

FIG. 4 is a diagram illustrating a function block of an ultrasound imaging apparatus according to the present invention. As shown in FIG. 4, the apparatus includes a detector 41, a processor 42, a display 43 or a printer 44. The detector 41 is used for measuring an object to obtain a reference image at a position and measuring the object having a deformation to obtain a deformed object image at the same position. The deformation of object can result from directly applying an external force or spontaneously producing. The processor 42 is employed for estimating an in-plane displacement field of the deformed object image for correcting an in-plane motion of the object to obtain a corrected image, compounding the reference image with the corrected image to obtain a compounded image of the object, and outputting a signal of the compounded image. The signal of the compounded image can be output into the display 43 or the printer 44. Thus, the compounded image can be shown in the display 43 or printed out by the printer 44.

Figure 5A:
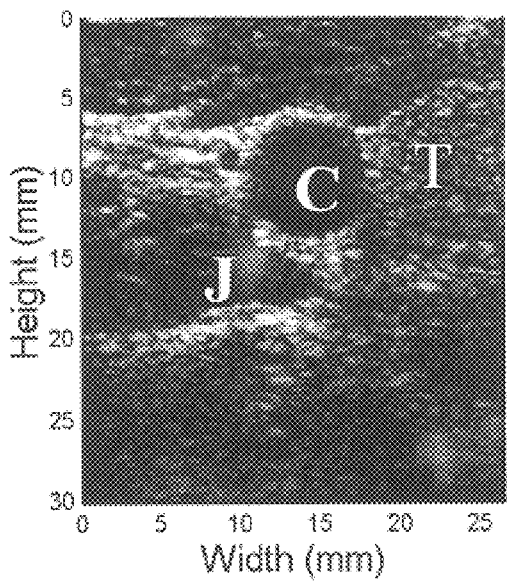
FIGS. 5A–5B are two images illustrating a thyroid image before and after compounding according to a preferred embodiment of the present invention.
Figure 5B:
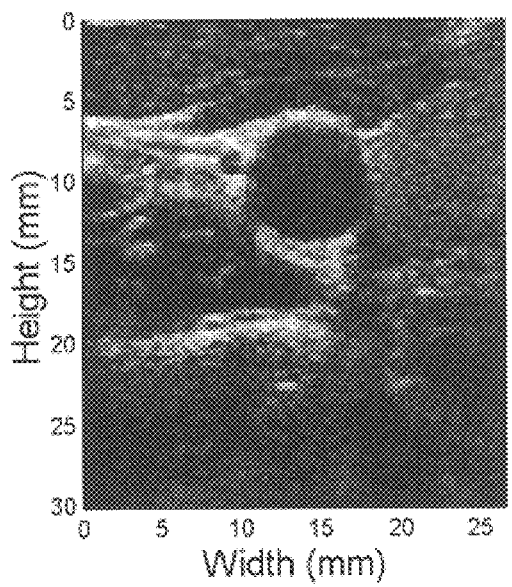

FIGS. 5A–5B are two images illustrating a thyroid image before and after compounding according to a preferred embodiment of the present invention. FIG. 5A is an image of thyroid (T), jugular vein (J) and carotid artery (C). FIG. 5B is a compound image of FIG. 5A by the compounding method of the present invention. Comparing the images between FIG. 5A and FIG. 5B, the speckle noise is apparently reduced and no noticeable degradation in spatial resolution is observed.

Accordingly, the compounding method of the present invention can be used in diagnostic ultrasound to improve low contrast detectability. It can also be applied to other imaging modalities with the presence of speckle. The present invention exploits the decorrelation between signals under different strain states, which can be created by externally applied forces or spontaneously motion, to further reduce the speckle noise. When such external forces are applied to the object, the object will produce three-dimensional object motion such as tissue motion and the images of the deformed object will be obtained. However, by correcting only the two-dimensional in-plane motion, the images under different strain states have identical characteristics except for the speckle appearance due to the un-corrected out-of-plane motion. Therefore, these images can be combined for speckle reduction without significantly affecting in-plane spatial resolution.

In sum, the compounding method according to the present invention is used for reducing speckle brightness variations of the image with less spatial resolution degradation. Thus, when the present invention applied in the diagnostic ultrasound, the low contrast detectability can be improved. In addition, the compounding method of the present invention can be implemented by free-hand scanning.

While the invention has been described in terms of what are presently considered to be the most practical and preferred embodiments, it is to be understood that the invention need not to be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A compounding method for reducing speckle noise applied in an ultrasound imaging apparatus, comprising the steps of:

providing an object;

measuring said object for obtaining a reference image by said ultrasound imaging apparatus;

applying an external force to said object to deform said object;

measuring said deformed object for obtaining a deformed object image at the same position;

estimating an in-plane displacement field of said deformed object image for correcting an in-plane motion of said object to obtain a corrected image; and compounding said reference image with said corrected image to obtain a compounded image of said object for achieving said speckle noise reduction.

2. The compounding method according to claim 1 wherein said ultrasound imaging apparatus is a medical diagnostic ultrasound apparatus.

3. The compounding method according to claim 1 wherein said object is selected from a group consisting of a tissue, an organ and an embryo.

4. The compounding method according to claim 1 wherein said reference image, said deformed object image, said corrected image and said compounded image are composed of a plurality of pixels, respectively.

5. The compounding method according to claim 4 wherein each said plural pixels of said compounded image is an average of each relative said plural pixels of said reference image and each relative said plural pixels of said corrected image, respectively.

6. A compounding method for reducing speckle noise applied in an ultrasound imaging apparatus, comprising the steps of:

providing an object which spontaneously produces deformation;

measuring said object for obtaining a first image at a first time;

measuring said object for obtaining a second image at a second time at same position, wherein said second image is an image of said deformed object;

estimating an in-plane displacement field of said second image for correcting an in-plane motion of said object to obtain a corrected image; and compounding said first image with said corrected image to obtain a compounded image of said object for achieving said speckle noise reduction.

7. The compounding method according to claim 6 wherein said ultrasound imaging apparatus is a medical diagnostic ultrasound apparatus.

8. The compounding method according to claim 6 wherein said object is selected from a group consisting of a tissue, an organ and an embryo.

9. The compounding method according to claim 6 wherein said first image, said second image, said corrected image and said compounded image are composed of a plurality of pixels, respectively.

10. The compounding method according to claim 9 wherein each said plural pixels of said compounded image is an average of each relative said plural pixels of said first image and each relative said plural pixels of said corrected image, respectively.

11. An ultrasound imaging apparatus, comprising:

a detector for measuring an object to obtain a reference image at a position and measuring said object having a deformation to obtain an deformed object image at said position; and a processor for estimating an in-plane displacement field of said deformed object image for correcting an in-plane motion of said object to obtain a corrected image, compounding said reference image with said corrected image to obtain a compounded image of said object for achieving speckle noise reduction, and outputting a signal of said compounded image.

12. The ultrasound imaging apparatus according to claim 11 wherein said ultrasound imaging apparatus is a medical diagnostic ultrasound apparatus.

13. The ultrasound imaging apparatus according to claim 11 wherein said object is selected from a group consisting of a tissue, an organ and an embryo.

14. The ultrasound imaging apparatus according to claim 11 wherein said deformation of said object is results from one of applying an external force and spontaneously producing.

15. The ultrasound imaging apparatus according to claim 11 wherein said reference image, said deformed object image, said corrected image and said compounded image are composed of a plurality of pixels, respectively.

16. The ultrasound imaging apparatus according to claim 15 wherein each said plural pixels of said compounded image is an average of each relative said plural pixels of said reference image and each relative said plural pixels of said corrected image, respectively.

17. The ultrasound imaging apparatus according to claim 11 further comprises a device for receiving said signal of said compounded image, wherein said device is one of a display and a printer.

* * * * *